United States Patent
Kuwabara

(10) Patent No.: US 11,272,896 B2
(45) Date of Patent: Mar. 15, 2022

(54) RADIOGRAPHIC IMAGE CAPTURING SYSTEM, PHANTOM, AND EVALUATION METHOD

(71) Applicant: FUJIFILM CORPORATION, Tokyo (JP)

(72) Inventor: Takao Kuwabara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 156 days.

(21) Appl. No.: 16/749,979

(22) Filed: Jan. 22, 2020

(65) Prior Publication Data

US 2020/0155104 A1    May 21, 2020

Related U.S. Application Data

(63) Continuation of application No. PCT/JP2018/028328, filed on Jul. 27, 2018.

(30) Foreign Application Priority Data

Jul. 27, 2017    (JP) .............................. JP2017-145849

(51) Int. Cl.
*G01N 29/30* (2006.01)
*H05G 1/64* (2006.01)
*A61B 6/00* (2006.01)

(52) U.S. Cl.
CPC ............ *A61B 6/5205* (2013.01); *A61B 6/481* (2013.01); *A61B 6/502* (2013.01); *A61B 6/548* (2013.01); *A61B 6/584* (2013.01)

(58) Field of Classification Search
CPC ....... A61B 6/5205; A61B 6/502; A61B 6/548; A61B 6/582; A61B 6/583; A61B 6/584
See application file for complete search history.

(56) References Cited

U.S. PATENT DOCUMENTS

| 5,299,253 A | 3/1994 | Wessels |
| 2006/0056580 A1* | 3/2006 | Frangioni ............ G01N 23/223 378/18 |

(Continued)

FOREIGN PATENT DOCUMENTS

| GB | 2445453 A | 7/2008 |
| JP | 2008-161690 A | 7/2008 |

(Continued)

OTHER PUBLICATIONS

Extended European Search Report dated Jun. 15, 2020, issued in corresponding EP Patent Application No. 18838992.8.

(Continued)

*Primary Examiner* — Don K Wong
(74) *Attorney, Agent, or Firm* — Solaris Intellectual Property Group, PLLC

(57) ABSTRACT

A radiographic image capturing system includes: a mammography apparatus that emits radiation having a first energy to a subject and captures a first radiographic image with a radiation detector and emits radiation having a second energy greater than the first energy to the subject and captures a second radiographic image with the radiation detector and that captures the first radiographic image and the second radiographic image with a breast in a state in which a contrast medium using iodine is administered. The radiographic image capturing system includes a phantom for evaluation of the mammography apparatus that has a solid material containing at least one element, which has a value of a k absorption edge that is equal to or greater than the first energy and equal to or less than the second energy, as an image evaluation pattern simulating the contrast medium.

3 Claims, 8 Drawing Sheets

(56) References Cited

U.S. PATENT DOCUMENTS

| | | |
|---|---|---|
| 2007/0025514 A1 | 2/2007 | Lawaczeck |
| 2008/0167552 A1 | 7/2008 | Bouchevreau et al. |
| 2012/0238870 A1 | 9/2012 | Smith et al. |
| 2013/0091966 A1 | 4/2013 | Hsu et al. |
| 2015/0327826 A1 | 11/2015 | Smith et al. |
| 2016/0128659 A1 | 5/2016 | Carton et al. |
| 2017/0042501 A1 | 2/2017 | Jahnke et al. |

FOREIGN PATENT DOCUMENTS

| | | |
|---|---|---|
| JP | 2008-541963 A | 11/2008 |
| JP | 2014-507250 A | 3/2014 |
| JP | 2016-523162 A | 8/2016 |

OTHER PUBLICATIONS

International Search Report issued in International Application No. PCT/JP2018/028328 dated Sep. 11, 2018.
Written Opinion of the ISA issued in International Application No. PCT/JP2018/028328 dated Sep. 11, 2018.
English language translation of the following: Office action dated Aug. 4, 2020 from the JPO in a Japanese patent application No. 2019-532890 corresponding to the instant patent application.
Office Action dated Mar. 23, 2021, issued by the EPO in corresponding EP Patent Application No. EP18838992.8.

\* cited by examiner ial Application No. PCT/JP2018/028328, filed Jul. 27,
RADIOGRAPHIC IMAGE CAPTURING SYSTEM, PHANTOM, AND EVALUATION METHOD

CROSS-REFERENCE TO RELATED APPLICATION

This application is a continuation application of International Application No. PCT/JP2018/028328, filed Jul. 27, 2018, the disclosure of which is incorporated herein by reference in its entirety. Further, this application claims priority from Japanese Patent Application No. 2017-145849 filed Jul. 27, 2017, the disclosure of which is incorporated herein by reference in their entirety.

BACKGROUND OF THE INVENTION

1. Field of the Invention

The present invention relates to a radiographic image capturing system, a phantom, and an evaluation method.

2. Description of the Related Art

A mammography apparatus is known that captures a radiographic image by emitting radiation from a radiation source toward the breast of a subject and detecting radiation transmitted through the breast using a radiation detector.

As this type of mammography apparatus, there is a mammography apparatus that can perform contrast imaging in which a breast in a state in which a contrast medium using iodine is administered is a subject. In addition, as a mammography apparatus capable of performing contrast imaging, a mammography apparatus is known in which radiation having a first energy is emitted and a first radiographic image is captured by a radiation detector and radiation having a second energy different from the first energy is emitted and a second radiographic image is captured by the radiation detector. In a case where this apparatus is used, a doctor examines a lesion part using a third radiographic image which is generated from the first radiographic image and the second radiographic image and in which a contrast medium is emphasized.

Incidentally, in general, evaluation (so-called quality control: QC) of a mammography apparatus is performed using a radiographic image captured with a phantom for evaluation as a subject. As this type of phantom, a contrast imaging phantom used for evaluating the contrast imaging function of a mammography apparatus is known. For example, JP2008-161690A discloses a phantom including a contrast medium insert.

SUMMARY OF THE INVENTION

In conventional contrast imaging phantoms, in the case of evaluating a mammography apparatus, users such as technicians may be troublesome to handling, such as preparing a phantom containing a contrast medium in a liquid state. For this reason, improvement of convenience for users has been desired.

The present disclosure has been made in consideration of the above circumstances, and provides a radiographic image capturing system, a phantom, and an evaluation method that can improve the convenience in evaluating the contrast imaging function of a mammography apparatus.

A radiographic image capturing system of a first aspect of the present disclosure comprises: a mammography apparatus that emits radiation having a first energy to a subject and captures a first radiographic image with a radiation detector and emits radiation having a second energy greater than the first energy to the subject and captures a second radiographic image with the radiation detector and that captures the first radiographic image and the second radiographic image with a breast in a state in which a contrast medium using iodine is administered; and a phantom for evaluation of the mammography apparatus that has a solid material containing at least one element, which has a value of a k absorption edge that is equal to or greater than the first energy and equal to or less than the second energy, as an image evaluation pattern simulating the contrast medium.

A radiographic image capturing system of a second aspect of the present disclosure comprises: a mammography apparatus that emits radiation having a first energy to a subject and captures a first radiographic image with a radiation detector and emits radiation having a second energy greater than the first energy to the subject and captures a second radiographic image with the radiation detector and that captures the first radiographic image and the second radiographic image with a breast in a state in which a contrast medium using iodine is administered; and a phantom for evaluation of the mammography apparatus that has a solid material containing at least one element, which has an atomic number of 45 to 56, as an image evaluation pattern simulating the contrast medium.

In the radiographic image capturing system of a third aspect of the present disclosure, a thickness of the solid material in an incidence direction of the radiation is a thickness determined according to a concentration of the contrast medium.

In the radiographic image capturing system of a fourth aspect of the present disclosure, the phantom further has another predetermined image evaluation pattern.

In the radiographic image capturing system of a fifth aspect of the present disclosure, the image evaluation pattern includes at least one of an image evaluation pattern for evaluating a contrast to noise ratio or an image evaluation pattern for evaluating low contrast detectability.

In the radiographic image capturing system of a sixth aspect of the present disclosure, the image evaluation pattern includes at least one of an image evaluation pattern simulating a mass, an image evaluation pattern simulating a microcalcification, or an image evaluation pattern simulating a fiber structure.

In the radiographic image capturing system of a seventh aspect of the present disclosure, the first energy is equal to or greater than 22 keV and less than a value of a k absorption edge of iodine, and the second energy is greater than the value of the k absorption edge of iodine and equal to or less than 49 keV.

In the radiographic image capturing system of an eighth aspect of the present disclosure, the solid material is molded by performing any of vapor deposition, sputtering, fine particle coating, and machining with respect to the element.

The radiographic image capturing system of a ninth aspect of the present disclosure further comprises: a generation unit that generates a third radiographic image in which the contrast medium is emphasized from the first radiographic image and the second radiographic image and that generates the third radiographic image in which the solid material is emphasized instead of the contrast medium in a case where the mammography apparatus captures the first radiographic image and the second radiographic image with the phantom as a subject.

The radiographic image capturing system of a tenth aspect of the present disclosure further comprises: an evaluation unit that evaluates the mammography apparatus based on the third radiographic image generated by the generation unit in a case where the phantom is a subject.

A phantom of an eleventh aspect of the present disclosure is a phantom for evaluation of a mammography apparatus comprising a solid material containing at least one element, which has a value of a k absorption edge that is equal to or greater than 22 keV and equal to or less than 49 keV, as an image evaluation pattern simulating a contrast medium using iodine.

A phantom of a twelfth aspect of the present disclosure is a phantom for evaluation of a mammography apparatus comprising a solid material containing at least one element, which has an atomic number of 45 to 56, as an image evaluation pattern simulating a contrast medium using iodine.

An evaluation method of a thirteenth aspect of the present disclosure is an evaluation method for a mammography apparatus, and comprises: a step in which a phantom for evaluation of the mammography apparatus having a solid material containing at least one element, which has a value of a k absorption edge that is equal to or greater than 22 keV and equal to or less than 49 keV, as an image evaluation pattern simulating a contrast medium using iodine is irradiated with radiation having a first energy from the mammography apparatus and a first radiographic image is captured by a radiation detector; a step in which the phantom is irradiated with radiation having a second energy greater than the first energy and a second radiographic image is captured by the radiation detector; and a step of generating a third radiographic image in which the solid material is emphasized from the first radiographic image and the second radiographic image.

An evaluation method of a fourteenth aspect of the present disclosure is an evaluation method for a mammography apparatus, and comprises: a step in which a phantom for evaluation of the mammography apparatus having a solid material containing at least one element, which has an atomic number of 45 to 56, as an image evaluation pattern simulating a contrast medium using iodine is irradiated with radiation having a first energy from the mammography apparatus and a first radiographic image is captured by a radiation detector; a step in which the phantom is irradiated with radiation having a second energy greater than the first energy and a second radiographic image is captured by the radiation detector; and a step of generating a third radiographic image in which the solid material is emphasized from the first radiographic image and the second radiographic image.

According to the present disclosure, an effect is obtained that the convenience in evaluating the contrast imaging function of the mammography apparatus can be improved.

DESCRIPTION OF THE PREFERRED EMBODIMENTS

Hereinafter, embodiments of the present invention will be described in detail with reference to the accompanying diagrams. In addition, the present embodiment does not limit the present invention.

First Embodiment

Figure 1:
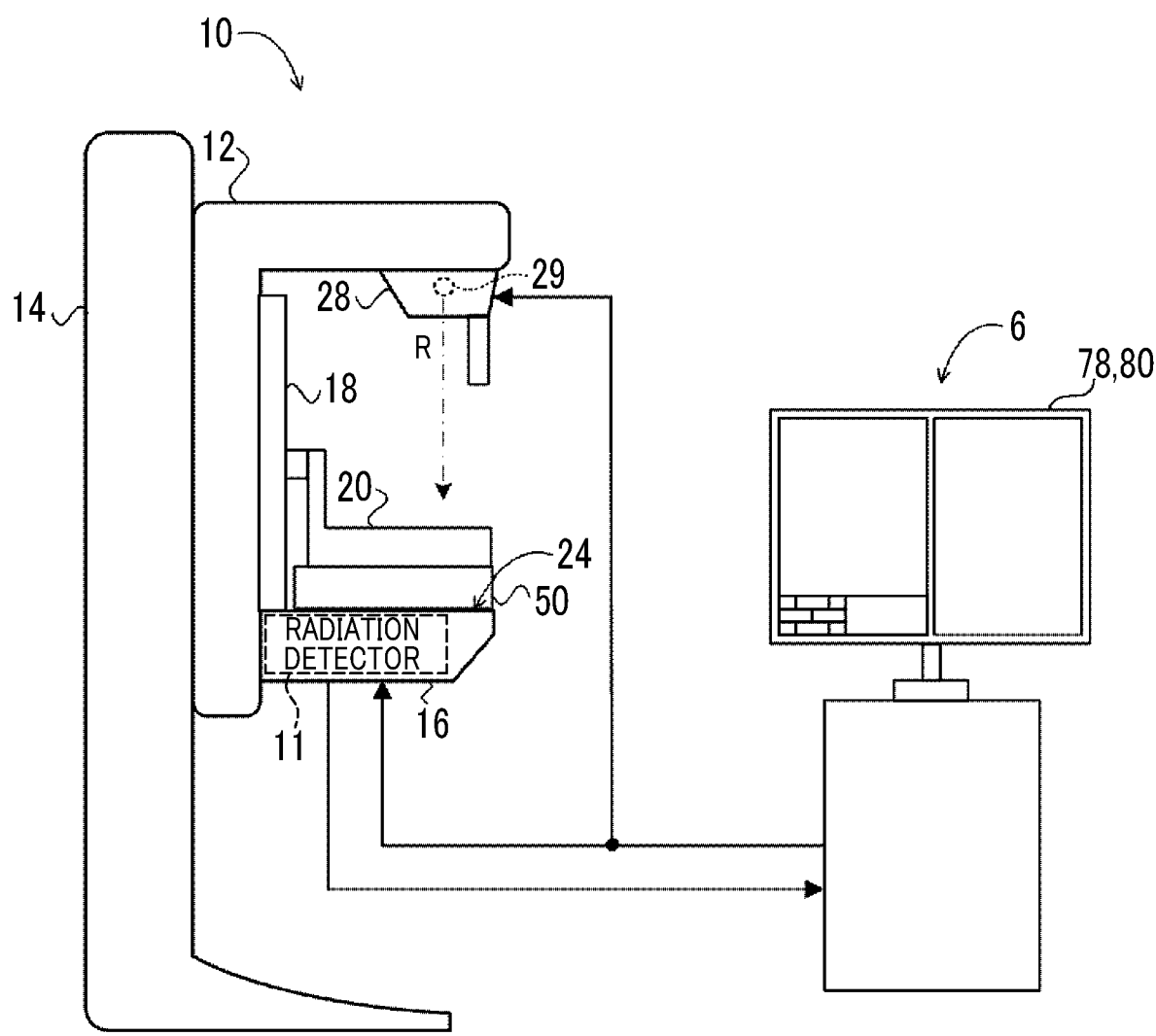
FIG. 1 is a configuration diagram schematically showing an example of the overall configuration of a radiographic image capturing system of a first embodiment.

First, an example of the overall configuration of a radiographic image capturing system of the present embodiment will be described. In FIG. 1, a configuration diagram showing an example of the overall configuration of a radiographic image capturing system 1 of the present embodiment is shown.

The radiographic image capturing system 1 of the present embodiment has a function of capturing a radiographic image by the operation of a user, such as a doctor or a radiology technician, based on an instruction (imaging order) input from an external system (for example, a radiology information system (RIS)) through the console 6.

Figure 2:
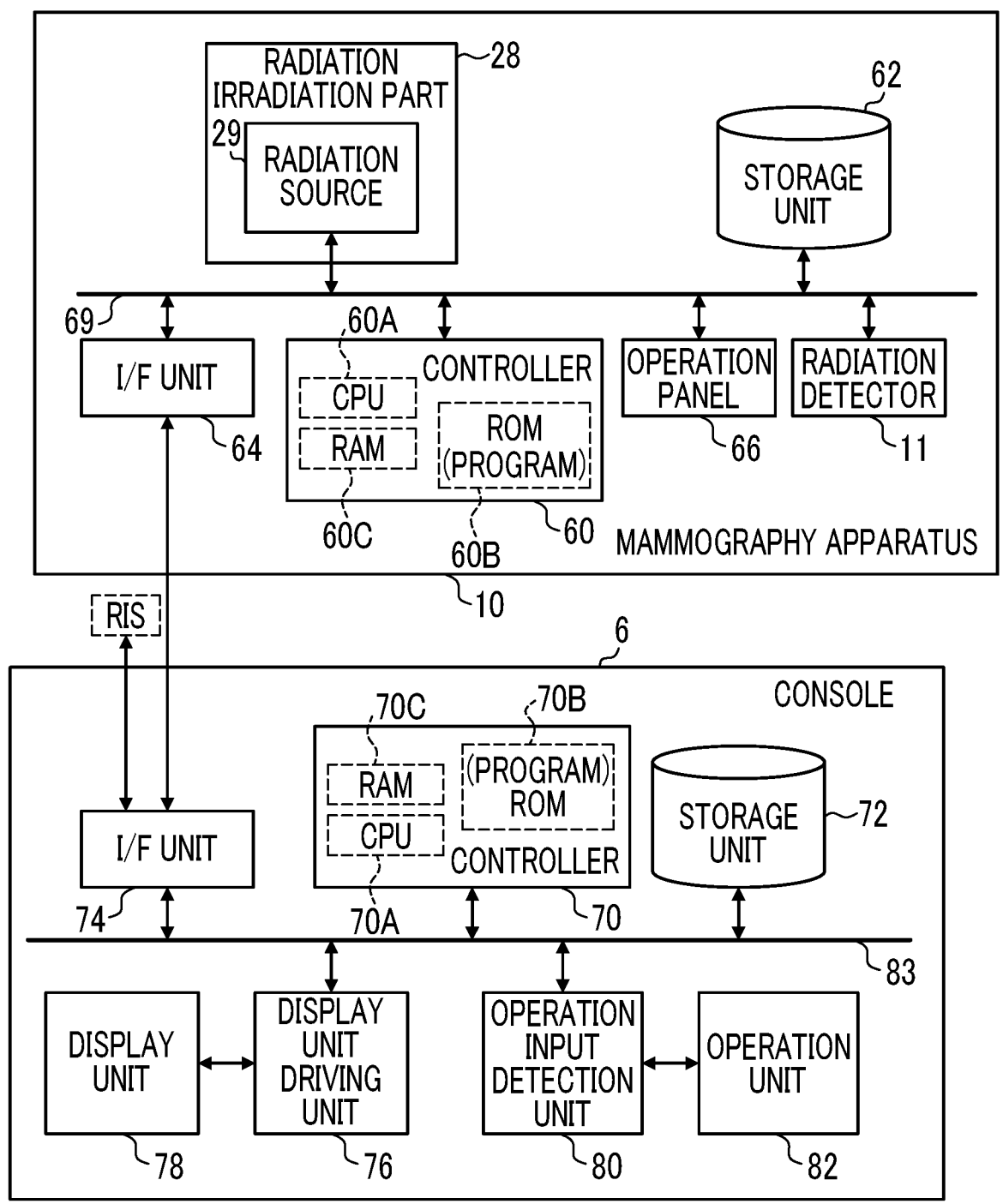
FIG. 2 is a block diagram showing an example of the configuration of a console and a mammography apparatus of the first embodiment.

As shown in FIG. 1, the radiographic image capturing system 1 of the present embodiment comprises a console 6, a mammography apparatus 10, and a phantom 50. In FIG. 2, a block diagram showing an example of the configuration of the console 6 and the mammography apparatus 10 of the present embodiment is shown.

The console 6 of the present embodiment has a function of controlling the mammography apparatus 10 using the imaging order or various kinds of information acquired from an external system or the like through a wireless communication local area network (LAN) or the like.

The console 6 of the present embodiment is a server computer as an example. As shown in FIG. 2, the console 6 comprises a controller 70, a storage unit 72, an interface (I/F) unit 74, a display unit driving unit 76, a display unit 78, an operation input detection unit 80, and an operation unit 82. The controller 70, the storage unit 72, the I/F unit 74, the display unit driving unit 76, and the operation input detection unit 80 are connected to each other through a bus 83, such as a system bus or a control bus, so that various kinds of information can be transmitted and received therebetween.

The controller 70 of the present embodiment controls the overall operation of the console 6. The controller 70 of the present embodiment comprises a central processing unit (CPU) 70A, a read only memory (ROM) 70B, and a random access memory (RAM) 70C. Various programs including an image evaluation processing program to be described later, which are executed by the CPU 70A, are stored in advance in the ROM 70B. The RAM 70C temporarily stores various kinds of data.

Image data of a radiographic image captured by the mammography apparatus 10, other various kinds of information, and the like are stored in the storage unit 72. In addition, the evaluation result of the mammography apparatus 10, which will be described in detail later, is stored in the storage unit 72 of the present embodiment. As specific examples of the storage unit 72, a hard disk drive (HDD), a solid state drive (SSD), and the like can be mentioned. The I/F unit 74 communicates with an external system, such as the mammography apparatus 10 or the RIS, by wireless communication or wired communication to transmit and receive various kinds of information therebetween.

The display unit 78 displays various kinds of information. The display unit driving unit 76 controls display of various kinds of information on the display unit 78. The operation unit 82 is used by the user to input various kinds of information, instructions regarding radiographic image capturing including a radiation R exposure instruction, and the like. The operation unit 82 is not particularly limited, and examples thereof include various switches, a touch panel, a touch pen, and a mouse. In addition, the operation unit 82 and the display unit 78 may be integrated to form a touch panel display. The operation input detection unit 80 detects an operation state with respect to the operation unit 82.

On the other hand, the mammography apparatus 10 of the present embodiment is an apparatus that captures a radiographic image of a breast as a subject by emitting radiation R (X-rays) to the breast of the subject. In addition, the mammography apparatus 10 may be an apparatus that images the breast of the subject not only in a state in which the subject is standing (standing state) but also in a state in which the subject is sitting on a chair (including a wheelchair) or the like (sitting state), and may be any apparatus capable of capturing at least a radiographic image of the breast of the subject.

In addition, the mammography apparatus 10 of the present embodiment has a contrast enhanced digital mammography (CEDM) function for performing contrast imaging by energy subtraction imaging as a function of performing imaging in a state in which a contrast medium is administered to the breast of the subject, so-called contrast imaging.

As shown in FIG. 2, the mammography apparatus 10 of the present embodiment comprises a radiation detector 11, a radiation emission unit 28 having a radiation source 29, a controller 60, a storage unit 62, an I/F unit 64, and an operation panel 66. The radiation detector 11, the radiation emission unit 28, the controller 60, the storage unit 62, the I/F unit 64, and the operation panel 66 are connected to each other through a bus 69, such as a system bus or a control bus, so that various kinds of information can be transmitted and received therebetween.

The controller 60 of the present embodiment controls the overall operation of the mammography apparatus 10. In addition, the controller 60 of the present embodiment controls the radiation detector 11 and the radiation emission unit 28 in the case of capturing a radiographic image. The controller 60 of the present embodiment comprises a CPU 60A, a ROM 60B, and a RAM 60C. Various programs including an imaging processing program to be described later, which are executed by the CPU 60A, are stored in advance in the ROM 60B. The RAM 60C temporarily stores various kinds of data.

Image data of a radiographic image captured by the radiation detector 11, other various kinds of information, and the like are stored in the storage unit 62. As specific examples of the storage unit 62, an HDD, an SSD, and the like can be mentioned. The I/F unit 64 communicates with the console 6 by wireless communication or wired communication to transmit and receive various kinds of information therebetween. The operation panel 66 is provided as a plurality of switches on an imaging table 16 of the mammography apparatus 10, for example. In addition, the operation panel 66 may be provided as a touch panel.

Figure 3:
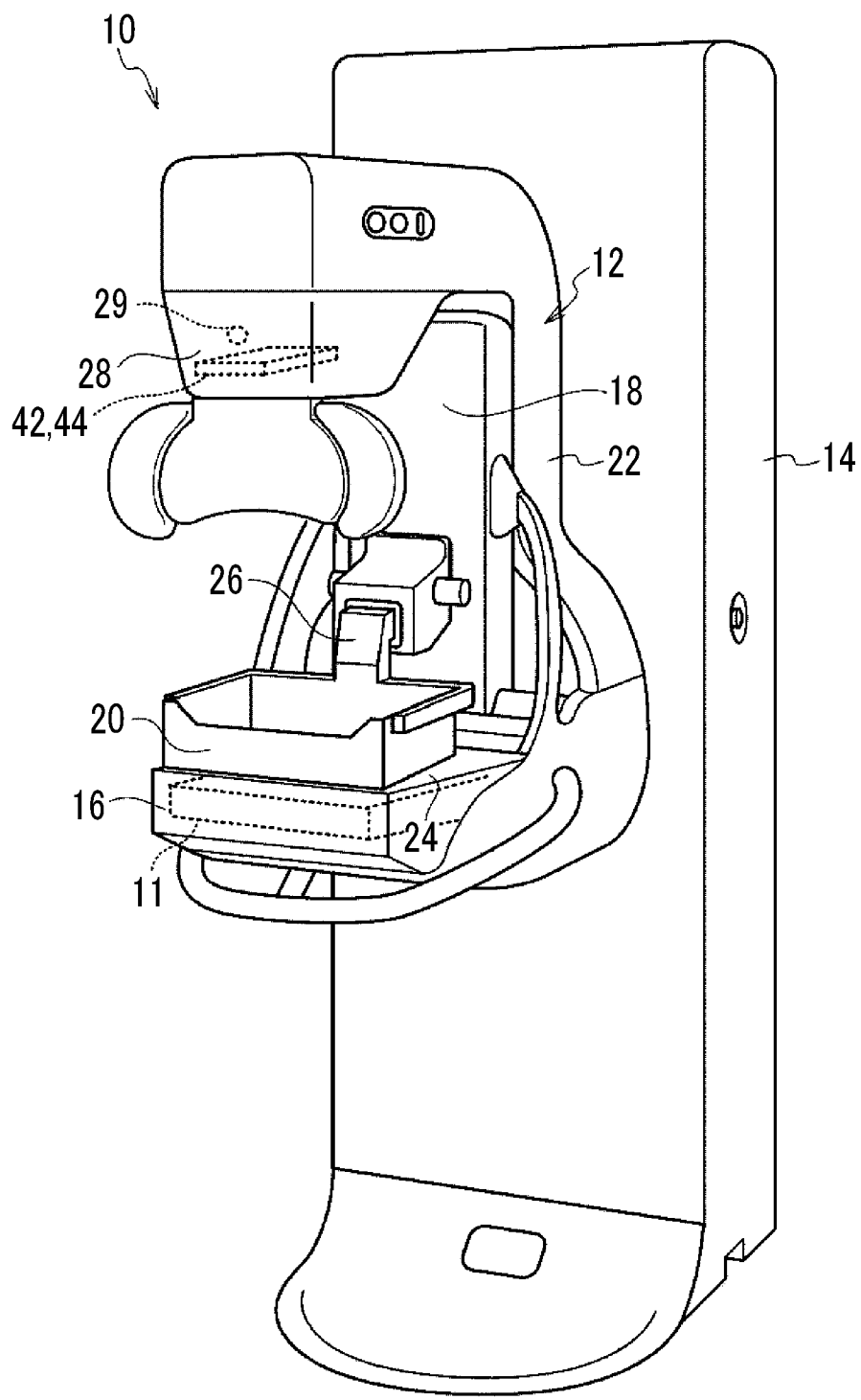
FIG. 3 is a perspective view in a case where an example of the overall configuration of the mammography apparatus of the first embodiment is viewed from the chest wall side of a subject.

In FIG. 3, a configuration diagram showing an example of the overall configuration of the mammography apparatus 10 of the present embodiment is shown. The following description will be given on the assumption that the side closer to the subject (chest wall side) in a case where the subject faces the mammography apparatus 10 in radiographic image capturing is the front side of the mammography apparatus 10 and the side away from the subject is the rear side of the mammography apparatus 10. In addition, the description will be given on the assumption that the left-right direction of the subject in a case where the subject faces the mammography apparatus 10 is the left-right direction of the mammography apparatus 10. In addition, the description will be given on the assumption that the head direction of the subject in a case where the subject faces the mammography apparatus 10 is the upper side and the foot direction is the lower side.

As shown in FIG. 3, the mammography apparatus 10 comprises an imaging unit 12, which has an approximately C shape in a side view and is provided on the front side of the apparatus, and a base unit 14 that supports the imaging unit 12 from the rear side of the apparatus.

The imaging unit 12 comprises the imaging table 16 having a planar imaging surface 24 in contact with the breast of the subject, a compression plate 20 for compressing the breast interposed between the compression plate 20 and the imaging surface 24 of the imaging table 16, and a holding unit 18 that supports the imaging table 16 and the compression plate 20. A member that transmits the radiation R is used as the compression plate 20. The imaging unit 12 comprises a support unit 22 that supports the radiation source 29 and the radiation emission unit 28, and the support unit 22 is separated from the holding unit 18.

As shown in FIG. 3, the radiation source 29 comprising a tube (tungsten as an example in the present embodiment) for emitting the radiation R to the breast is provided inside the radiation emission unit 28 of the mammography apparatus 10 of the present embodiment. In the radiation emission unit 28, a rhodium (Rh) filter 42 and a copper (Cu) filter 44 are provided between the radiation source 29 and the imaging table 16. In FIG. 3, the Rh filter 42 and the Cu filter 44 are shown as being integrated, but the filters are provided as separate filters.

The filters provided in the mammography apparatus 10 are not limited to the Rh filter 42 and the Cu filter 44. For example, a molybdenum (Mo) filter may be provided instead of the Rh filter 42 or in addition to the Rh filter 42. In addition, for example, an aluminum (Al) filter has a lower radiation R attenuation rate than the Rh filter 42. Therefore, the Al filter is suitable for tomosynthesis imaging in which the imaging time (radiation R emission time) at each imaging position in a state in which the radiation source 29 is continuously moved is short. For this reason, in a case where the mammography apparatus 10 has a function of performing tomosynthesis imaging, an Al filter may be provided and tomosynthesis imaging may be performed using the Al filter.

A moving unit (not shown) is provided inside the radiation emission unit 28. In the case of capturing a radiographic image, the Rh filter 42 or the Cu filter 44 is moved to a position in the irradiation field according to the energy of the radiation R to be emitted.

On the other hand, a shaft (not shown) is provided in the imaging unit 12 of the present embodiment, so that the imaging unit 12 can rotate with respect to the base unit 14. The shaft is fixed to the support unit 22, so that the shaft and the support unit 22 rotate together. A gear is provided in each of the holding unit 18 and the shaft provided in the imaging unit 12. By switching the engagement state and the non-engagement state of the gears, it is possible to perform switching between a state in which the holding unit 18 and the shaft are connected to each other to rotate together and a state in which the shaft is separated from the holding unit 18 and idles. In addition, switching between transmission and non-transmission of the power of the shaft is not limited to the gear, and various mechanical elements can be used.

The holding unit 18 supports the imaging table 16 and the radiation source 29 by separating the imaging surface 24 and the radiation source 29 from each other by a predetermined distance. In addition, the holding unit 18 also holds the compression plate 20 through a support arm 26. The holding unit 18 makes the support arm 26 slide so that the compression plate 20 moves, and accordingly, the distance between the compression plate 20 and the imaging surface 24 changes.

The imaging surface 24 with which the breast of the subject comes into contact is formed of, for example, carbon from the viewpoint of radiolucency or strength. The radiation detector 11 that detects the radiation R transmitted through the breast and the imaging surface 24 is disposed in the imaging table 16. A radiographic image is generated based on the radiation R detected by the radiation detector 11. The type of the radiation detector 11 of the present embodiment is not particularly limited. For example, an indirect conversion type radiation detector that converts the radiation R into light and converts the converted light into electric charge may be used, or a direct conversion type radiation detector that converts the radiation R into electric charge may be used. In the present embodiment, image data indicating a radiographic image output from the radiation detector 11 of the mammography apparatus 10 is transmitted to the console 6.

As described above, the mammography apparatus 10 of the present embodiment has a function of performing contrast imaging. As a contrast medium used for contrast imaging, a contrast medium using iodine having a k absorption edge of 33 keV (hereinafter, simply referred to as a "contrast medium") is generally used. The mammography apparatus 10 captures a first radiographic image with the radiation detector 11 by emitting the radiation R having a first energy lower than the k absorption edge of the contrast medium to the breast as a subject to which the contrast medium has been administered, and captures a second radiographic image with the radiation detector 11 by emitting the radiation R having a second energy higher than the k absorption edge of the contrast medium to the breast as a subject to which the contrast medium has been administered.

In the mammography apparatus 10 of the present embodiment, emitting the radiation R having the first energy refers to emitting the radiation R from the radiation source 29 by applying a tube voltage of the first energy. Similarly, emitting the radiation R having the second energy refers to emitting the radiation R from the radiation source 29 by applying a tube voltage of the second energy.

The specific first energy and second energy are determined from the viewpoint of the specifications of the mammography apparatus 10, the desired image quality of the radiographic image, exposure of the subject, and the like in addition to the k absorption edge of the contrast medium. In general, the specific first energy and second energy are preferably 22 keV to 49 keV. In other words, it is preferable that the first energy is equal to or greater than 22 keV and less than the value of the k absorption edge of the contrast medium. In addition, it is preferable that the second energy is greater than the value of the k absorption edge of the contrast medium and equal to or less than 49 keV.

In the mammography apparatus 10 of the present embodiment, the first energy is the same as the energy of the radiation R used for normal (general) imaging. In the mammography apparatus 10, in the case of performing imaging by emitting the radiation R having the first energy (hereinafter, referred to as "first imaging"), the Rh filter 42 is disposed in the irradiation field. Since the k absorption edge of Rh is 23.2 keV, the quality of the radiation R emitted to the subject is a radiation quality in which an energy component of 23.2 keV or more is suppressed.

In the mammography apparatus 10 of the present embodiment, the second energy is set in the range of 45 keV to 49 keV. In the mammography apparatus 10, in the case of performing imaging by emitting the radiation R having the second energy (hereinafter, referred to as "second imaging"), the Cu filter 44 is disposed in the irradiation field. The k absorption edge of Cu is as low as 9.0 keV. However, by setting the thickness appropriately, the quality of the radiation R emitted to the subject can be made to be a radiation quality in which the first energy component of the radiation R is suppressed.

The first radiographic image captured by the first imaging and the second radiographic image captured by the second imaging are output to the console 6, and the console 6 calculates the concentration distribution of the contrast medium from the difference between the pieces of image data of the first radiographic image and the second radiographic image and images the contrast medium. Specifically, the controller 70 of the console 6 of the present embodiment generates image data of a difference image, in which the human body structure is suppressed and the administered contrast medium is emphasized, by subtracting image data, which is obtained by multiplying the image data of the first radiographic image by a first coefficient set in advance, from image data, which is obtained by multiplying the image data of the second radiographic image by a second coefficient set in advance. The difference image generation method of the controller 70 is not limited thereto, and a known difference image generation method can be used. The difference image generated by the mammography apparatus 10 of the present embodiment is an example of a third radiographic image of the present disclosure.

Figure 4:
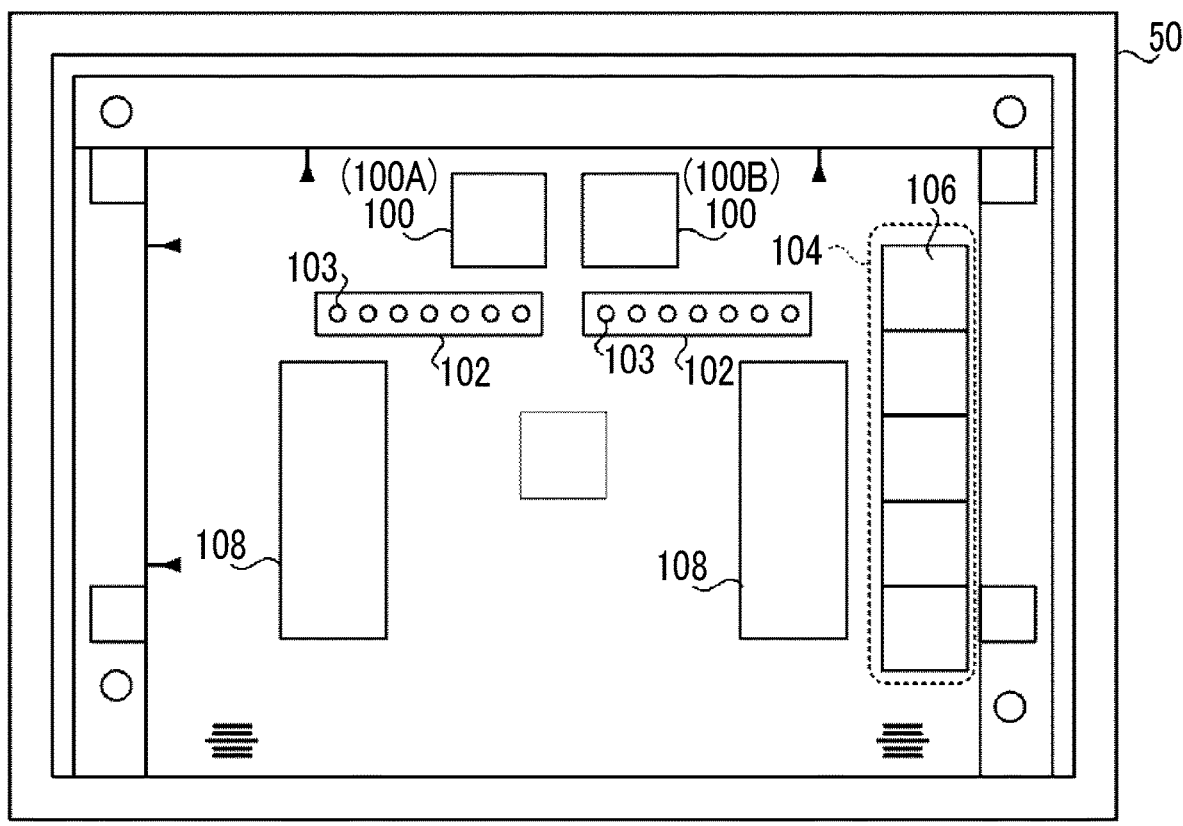
FIG. 4 is a plan view seen from the radiation source side showing the configuration of an example of a phantom of the first embodiment.

On the other hand, the phantom 50 of the present embodiment is used to evaluate the mammography apparatus 10 by evaluating the quality of a radiographic image based on desired image quality evaluation items. As an example, the phantom 50 of the present embodiment is applied to the method of international electrotechnical commission (IEC) and the method of European reference organization for quality assured breast screening and diagnostic services (EUREF). Specifically, the phantom 50 of the present embodiment additionally has a function of evaluating the detectability of a contrast medium image. FIG. 4 shows a plan view in a case where an example of the phantom 50 of the present embodiment is viewed from the radiation source 29 side.

As shown in FIG. 4, the phantom 50 of the present embodiment has an image evaluation pattern 100 and an image evaluation pattern 102 that are used for the evaluation of the detectability of a contrast medium image (hereinafter, simply referred to as "detectability of a contrast medium"). By including the image evaluation pattern 100 and the image evaluation pattern 102, image quality evaluation items of the phantom 50 of the present embodiment includes the detectability of the contrast medium.

In addition, although details will be described later, the image evaluation pattern 100 is also used for the evaluation of the contrast to noise ratio (CNR), which is one of the image quality evaluation items. In addition, although details will be described later, the image evaluation pattern 102 includes a plurality of disks 103, and is also used for the evaluation of the low contrast detectability (LCD), which is one of the image quality evaluation items.

In order to be used for the evaluation of the detectability of the contrast medium, the image evaluation pattern 100 and the image evaluation pattern 102 are formed as solid materials each having a predetermined size, shape, and density, which simulates a contrast medium, on a substrate formed of plastic (hereinafter referred to as a "plastic substrate"), such as poly ethylene terephthalate (PET) or polycarbonate. In the present embodiment, the "solid material" means that the shape does not change according to the shape of a container in which the solid is housed and the shape does not change with time.

The phantom 50 of the present embodiment has, as the image evaluation pattern 100 and the image evaluation pattern 102 simulating a contrast medium, a solid material containing at least one element having a k absorption edge within the range of the first energy to the second energy of the radiation R emitted from the radiation source 29.

In other words, in the phantom 50 of the present embodiment, the image evaluation pattern 100 and the image evaluation pattern 102 are formed as solid materials simulating a contrast medium by a material containing at least one element having a k absorption edge that is greater than the k absorption edge of the Rh filter 42 used in the first imaging, in which the radiation R having the first energy is emitted, and smaller than the peak energy of the radiation R in the second imaging.

Examples of this type of element include elements ranging from Rh having an atomic number of 45 and a k absorption edge of 23.2 keV to barium (Ba) having an atomic number of 56 and a k absorption edge of 37.4 keV. As for which of these elements is used, it is possible to appropriately use an element by which the image evaluation pattern 100 and an image evaluation pattern 102 can be easily formed (processed) in desired shapes and the like.

Examples of the solid material using this kind of element include a tin foil formed of Sn having an atomic number of 50 and a k absorption edge of 29.2 keV and an indium tin oxide (ITO) film formed of Sn and indium (In) having an atomic number of 49 and a k absorption edge of 27.9 keV.

In a case where the solid material is a tin foil, the image evaluation pattern 100 and the image evaluation pattern 102 can be formed on a plastic substrate by machining. For example, the image evaluation pattern 100 is formed in a rectangular shape having a thickness of 300 and a side of 3 cm. In addition, for example, in the image evaluation pattern 102, the disk 103 is formed in a circular shape having a thickness of 50 μm and a diameter of 2 mm.

On the other hand, in a case where the solid material is an ITO film, the image evaluation pattern 100 and the image evaluation pattern 102 can be formed on a plastic substrate using any method, such as vapor deposition, sputtering, and fine particle coating. For example, the image evaluation pattern 100 is formed in a rectangular shape having a thickness of 500 and a side of 3 cm. In addition, for example, in the image evaluation pattern 102, the disk 103 is formed in a circular shape having a thickness of 100 μm and a diameter of 2 mm. In addition, since the ITO film as the image evaluation pattern 100 and the image evaluation pattern 102 does not require transparency unlike in the case of being used as a transparent electrode, the film forming conditions are relatively loose and no heat treatment is required. Therefore, it is easy to increase the thickness of the ITO film, and it is possible to easily form a film on a plastic substrate.

The thickness of the image evaluation pattern 100 and the image evaluation pattern 102, specifically, the thickness in an incidence direction in which the radiation R is incident is determined according to the concentration of the contrast medium to be simulated, and the thickness in the incidence direction increases as the concentration of the contrast medium increases.

The phantom 50 of the present embodiment has image evaluation patterns for evaluating other desired image quality evaluation items. For example, as shown in FIG. 4, the phantom 50 has an image evaluation pattern 104 used for the evaluation of a dynamic range, an image evaluation pattern 106 used for the evaluation of linearity, and an image evaluation pattern 108 used for the evaluation of spatial resolution (SR).

Although details are omitted, the phantom 50 shown in FIG. 4 can further evaluate, for example, chest wall defect, system sensitivity invariance, geometric distortion, image unevenness (system artifact), and image uniformity as other desired image quality evaluation items, and has respective image evaluation patterns.

Figure 5:
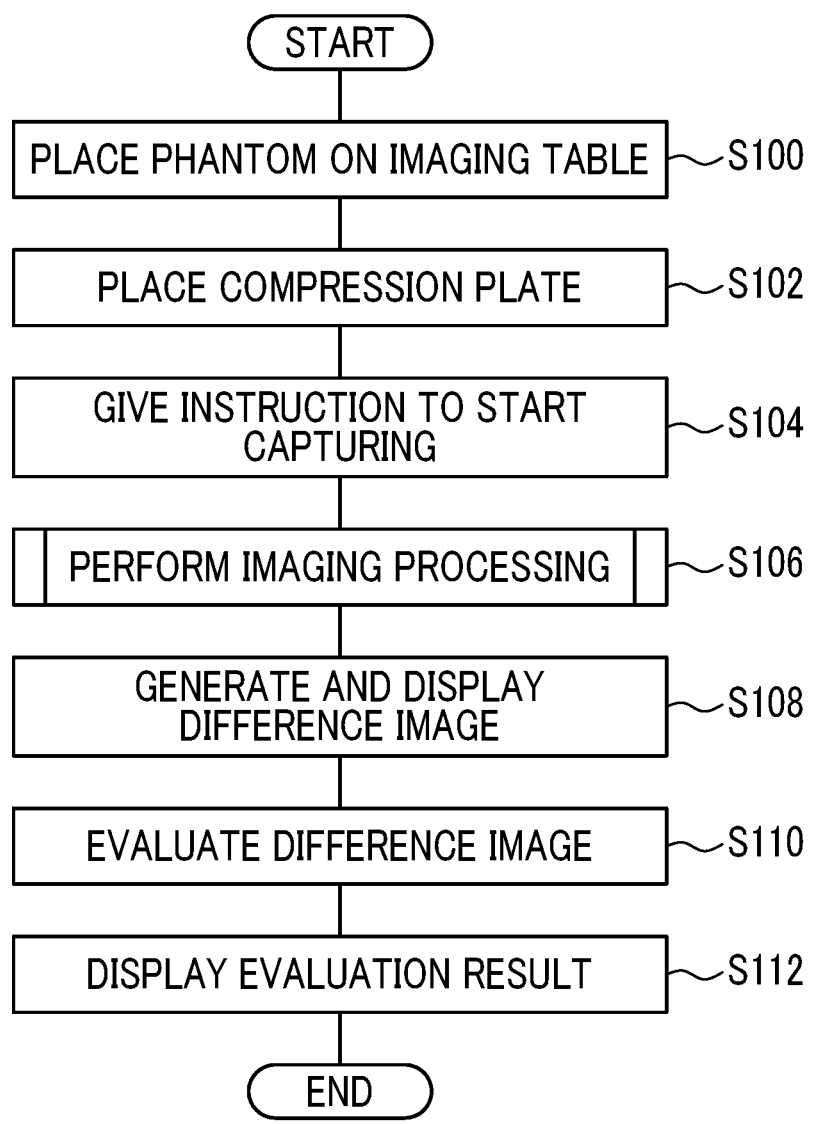
FIG. 5 is a flowchart showing an example of the flow of the entire evaluation operation of the mammography apparatus in the radiographic image capturing system of the first embodiment.

Next, an operation for evaluating the mammography apparatus 10 (hereinafter, referred to as an "evaluation operation") in the radiographic image capturing system 1 of the present embodiment will be described. FIG. 5 shows a flowchart showing an example of the flow of the entire evaluation operation by the radiographic image capturing system 1 of the present embodiment.

First, in step S100, the user places the phantom 50 as a subject at a certain position on the imaging surface 24 of the imaging table 16 of the mammography apparatus 10. Then, in the next step S102, the user places the compression plate 20 on the phantom 50.

In the next step S104, the user gives an instruction to start capturing a radiographic image from the operation unit 82 of the console 6. The instruction to start imaging (imaging start instruction) is transmitted to the mammography apparatus 10 through the I/F unit 74. In the radiographic image capturing system 1 of the present embodiment, the imaging order is also transmitted from the console 6 to the mammography apparatus 10 through the I/F unit 74.

Figure 6:
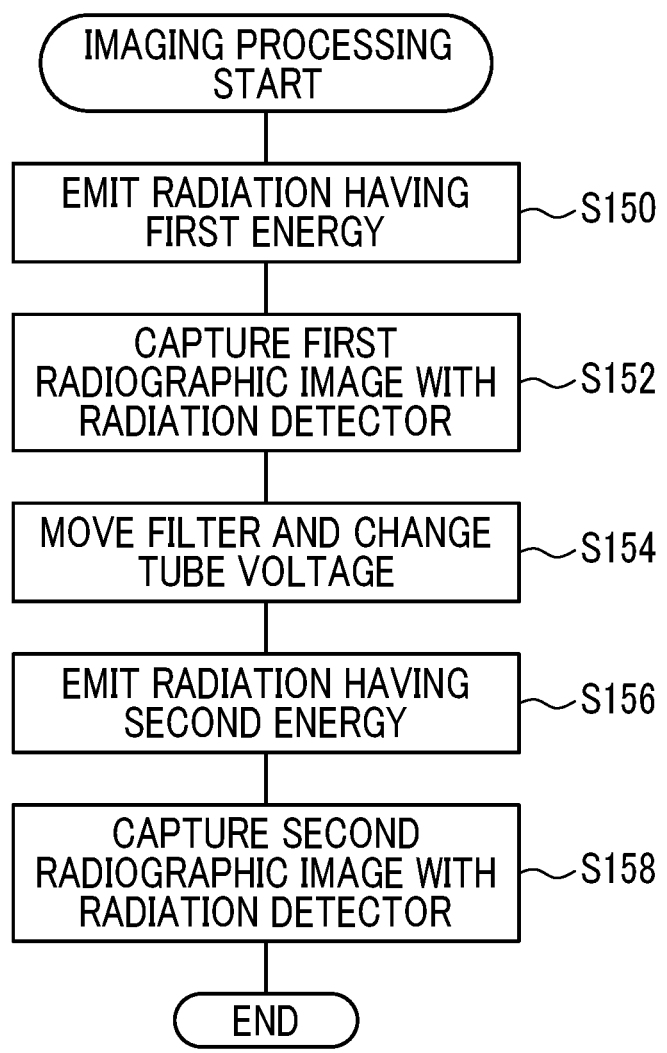
FIG. 6 is a flowchart showing an example of the flow of imaging processing performed by the mammography apparatus of the first embodiment.

In the next step S106, the mammography apparatus 10 performs imaging processing shown as an example in FIG. 6 to capture a radiographic image of the phantom 50. Thus, in the mammography apparatus 10 of the present embodiment, in a case where the imaging order and the instruction to start capturing a radiographic image are received from the console 6, the CPU 60A of the controller 60 executes an imaging processing program stored in the ROM 60B, thereby performing the imaging processing shown in FIG. 6.

As shown in FIG. 6, in step S150, the controller 60 of the mammography apparatus 10 emits the radiation R having a first energy from the radiation source 29. In the next step S152, the controller 60 performs the first imaging by capturing the first radiographic image with the radiation detector 11. In the present embodiment, the Rh filter 42 is disposed in the irradiation field in a state in which the imaging processing has started, at least in the case of performing the first imaging.

In steps S150 and S152, the radiation R having the first energy is emitted to the phantom 50, and image data indicating the first radiographic image generated by the radiation detector 11 according to the radiation R transmitted through the phantom 50 is output from the mammography apparatus 10 to the console 6.

In the next step S154, the controller 60 moves the Rh filter 42 and the Cu filter 44 to locate the Cu filter 44 in the irradiation field. In addition, the controller 60 changes a tube voltage applied to the radiation source 29 so as to be increased from the tube voltage in the case of emitting the first energy to the tube voltage in the case of emitting the second energy.

In the next step S156, the controller 60 emits the radiation R having a second energy from the radiation source 29. In the next step S158, the controller 60 performs the second imaging by capturing the second radiographic image with the radiation detector 11, and ends this imaging processing. In steps S156 and S158, the radiation R having the second energy is emitted to the phantom 50, and image data indicating the second radiographic image generated by the radiation detector 11 according to the radiation R transmitted through the phantom 50 is output from the mammography apparatus 10 to the console 6. Hereinafter, in a case where various radiographic images, such as the first radiographic image and the second radiographic image, are collectively called, these will be referred to as "radiographic images".

In a case where image data indicating a radiographic image captured by imaging processing is input from the mammography apparatus 10, the console 6 temporarily stores the input image data indicating the radiographic image in the storage unit 72.

In a case where the imaging processing of the mammography apparatus 10 in step S106 is ended as described above, the controller 70 of the console 6 generates a difference image from the first radiographic image and the second radiographic image and displays the difference image on the display unit 78 in the next step S108. Here, the method of generating a difference image is the same as a method of generating a difference image in the case of performing normal contrast imaging in a case where the breast in a state in which a contrast medium is administered is a subject. The controller 70 of the present embodiment is an example of a generation unit of the present disclosure.

Specifically, first, the controller 70 acquires image data indicating the first radiographic image and image data indicating the second radiographic image from the storage unit 72. Then, the controller 70 generates image data of a difference image by subtracting image data, which is obtained by multiplying the image data indicating the first radiographic image by a first coefficient set in advance, from image data, which is obtained by multiplying the image data indicating the second radiographic image by a second coefficient set in advance, for each corresponding pixel. The difference image generation method of the controller 70 is not limited thereto, and a known difference image generation method can be used.

In the next step S110, the controller 70 evaluates the generated difference image. The difference image evaluation method is not particularly limited, but an evaluation value CNR for evaluating the contrast to noise ratio using the image evaluation pattern 100 is obtained by the following Equation (1). In the following Equation (1), the average pixel value of the image of the image evaluation pattern 100 (100A) is $m_{AL}$, the standard deviation is $\sigma_{AL}$, the average pixel value of the image of the image evaluation pattern 100 (100B) is $m_{BG}$, and the standard deviation is $\sigma_{BG}$.

[Equation 1]

$$CNR = \frac{m_{BG} - m_{AL}}{\sqrt{\frac{\sigma_{BG}^2 + \sigma_{AL}^2}{2}}} \qquad (1)$$

In the radiographic image capturing system 1 of the present embodiment, the controller 70 derives the evaluation value CNR based on the image data of the difference image using the above Equation (1).

In addition, the LCD score for evaluating the low contrast detectability using the image evaluation pattern 102 is derived by a dot pattern (LCD pattern) formed in the difference image by the disk 103. In the difference image of the embodiment, white and black LCD patterns are formed by the disk 103 of the image evaluation pattern 102. The controller 70 digitizes the LCD score by deriving a function of cross correlation with the LCD pattern of the difference image using an ideal LCD pattern in a case where no noise is generated.

In the present embodiment, the CPU 70A executes an image evaluation processing program stored in the ROM 70B of the controller 70, so that the evaluation value CNR is derived and the LCD score is derived. In addition, the CPU 70A executes the image evaluation processing program, so that the controller 70 functions as an example of an evaluation unit of the present disclosure.

In addition, the detectability of the contrast medium by the image evaluation pattern 100 and the image evaluation pattern 102 in the radiographic image capturing system 1 of the present embodiment is evaluated based on the visual recognition result (visibility) of the user who views the difference image. Information indicating the evaluation based on the visual recognition result is input to the console 6 of the present embodiment by the user.

In the next step S112, the controller 70 displays the evaluation result of the difference image obtained in the above step S110 on the display unit 78. The console 6 of the present embodiment stores the evaluation result in the storage unit 72. In the radiographic image capturing system 1 of the present embodiment, the evaluation operation ends in a case where step S112 ends.

Second Embodiment

In the present embodiment, the configuration and the operation are the same except that the phantom 50 provided in the radiographic image capturing system 1 is different from the phantom 50 (refer to FIG. 4) of the first embodiment. Accordingly, the phantom 50 of the present embodiment will be described with the detailed description being omitted.

Figure 7:
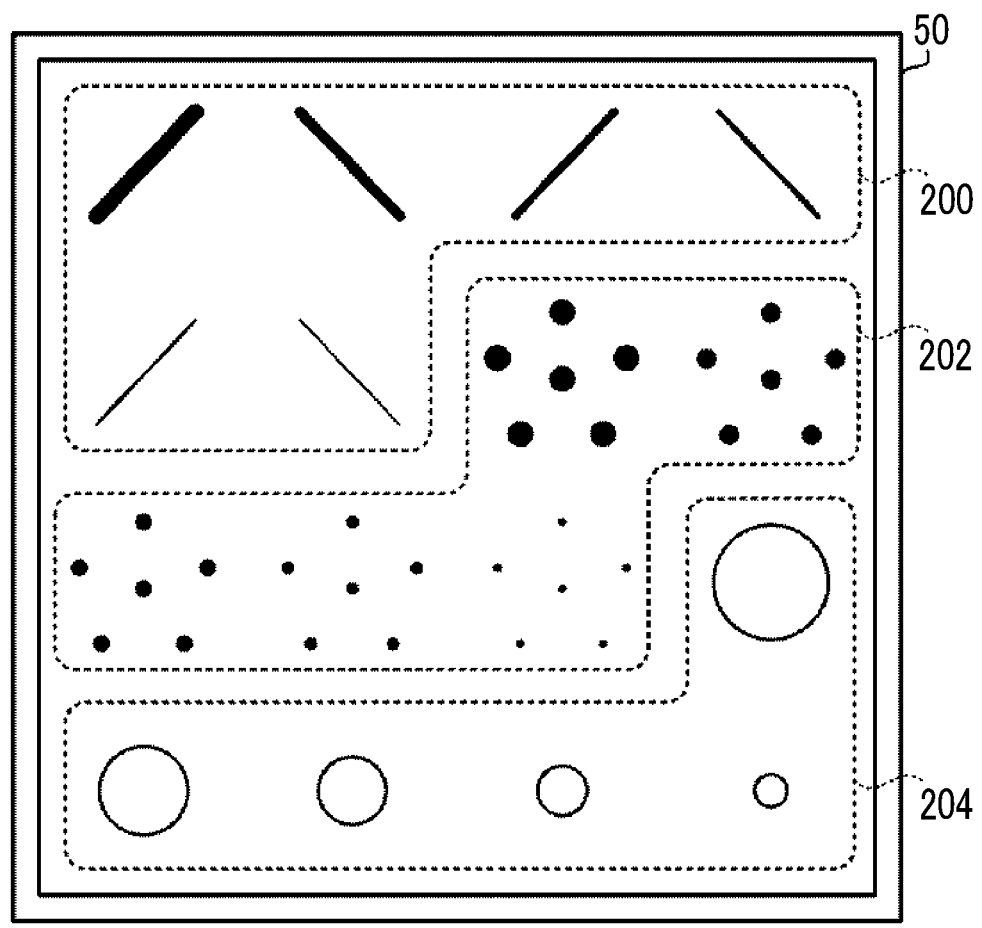
FIG. 7 is a plan view seen from the radiation source side showing the configuration of an example of a phantom of a second embodiment.

As described above, the phantom 50 of the first embodiment additionally has a function of evaluating the detectability of the contrast medium image. On the other hand, the phantom 50 of the present embodiment additionally has a function of visually evaluating the detectability of the contrast medium image. FIG. 7 shows a plan view in a case where an example of the phantom 50 of the present embodiment is viewed from the radiation source 29 side.

As shown in FIG. 4, the phantom 50 of the present embodiment has an image evaluation pattern 200, an image evaluation pattern 202, and an image evaluation pattern 204 that are used for the evaluation of the detectability of the contrast medium. By including the image evaluation pattern 200, the image evaluation pattern 202, and the image evaluation pattern 204, image quality evaluation items of the phantom 50 of the present embodiment includes the detectability of the contrast medium.

The image evaluation pattern 200 is also used for the evaluation of the detectability of a fiber structure (fiber), which is one of the image quality evaluation items. Therefore, the image evaluation pattern 200 includes a plurality of test objects having different sizes simulating a fiber structure. In the present embodiment, in order to be used for the evaluation of the detectability of the contrast medium, as an example, the image evaluation pattern 200 is created by molding a resin kneaded with barium sulfate powder as a solid material having a shape simulating a fiber structure with a desired size. The amount of barium sulfate kneaded into the resin (the content of barium sulfate) is determined according to the concentration of the contrast medium to be simulated, and the content of barium sulfate increases as the concentration of the contrast medium increases.

In addition, the image evaluation pattern 202 is also used for the evaluation of the detectability of microcalcification (calc), which is one of the image quality evaluation items. Therefore, the image evaluation pattern 202 includes a plurality of test objects having different sizes simulating a microcalcification. In the present embodiment, in order to be used for the evaluation of the detectability of the contrast medium, as an example, the image evaluation pattern 202 is created by molding a resin kneaded with barium sulfate powder as a solid material having a shape simulating a microcalcification with a desired size.

In addition, the image evaluation pattern 204 is also used for the evaluation of the detectability of a mass, which is one of the image quality evaluation items. Therefore, the image evaluation pattern 204 includes a plurality of test objects having different sizes simulating a mass. In the present embodiment, in order to be used for the evaluation of the detectability of the contrast medium, as an example, the image evaluation pattern 204 is created by molding and sintering barium sulfate powder into a solid material having a shape simulating a mass with a desired size.

The image evaluation pattern 200, the image evaluation pattern 202, and the image evaluation pattern 204 are built into a wax simulating the compressed breast.

The flow of the entire evaluation operation of the mammography apparatus 10 using the phantom 50 of the present embodiment is the same as the flow of the entire evaluation operation (refer to FIG. 5) of the first embodiment. Needless to say, in the evaluation of the difference image in step S110 in the flow of the entire evaluation operation, evaluation according to the image evaluation pattern 200, the image evaluation pattern 202, and the image evaluation pattern 204 is performed.

Specifically, the detectability of the contrast medium in a case where the phantom 50 of the present embodiment is evaluated based on the visual recognition result (visibility) of the user who views the difference image. In addition, the detectability of the fiber structure, the mass, and the microcalcification is also evaluated based on the visual recognition result (visibility) of the user who views the difference image.

In the present embodiment, the form has been described in which each of the image evaluation pattern 200, the image evaluation pattern 202, and the image evaluation pattern 204 is used for the evaluation of the detectability of the contrast medium. However, any one or more image evaluation patterns may be used for the evaluation of the detectability of the contrast medium. For example, the image evaluation pattern 202 may be used for the evaluation of the detectability of the microcalcification and the detectability of the contrast medium, and the image evaluation pattern 200 and the image evaluation pattern 204 may be respectively used only for the evaluation of the detectability of the fiber structure and the detectability of the mass.

As described above, the radiographic image capturing system 1 of each of the embodiments described above comprises the mammography apparatus 10 that emits the radiation R having the first energy to the subject and captures a first radiographic image with the radiation detector 11 and emits the radiation R having the second energy greater than the first energy to the subject and captures a second radiographic image with the radiation detector 11 and that captures the first radiographic image and the second radiographic image with the breast in a state in which a contrast medium using iodine is administered. In addition, the radiographic image capturing system 1 comprises the phantom 50 for evaluation of the mammography apparatus 10 that has a solid material containing at least one element, which has a value of the k absorption edge that is equal to or greater than the first energy and equal to or less than the second energy, as an image evaluation pattern simulating the contrast medium.

In other words, for the phantom 50, the radiographic image capturing system 1 of each of the above embodiments comprises the phantom 50 for the evaluation of the mammography apparatus 10 having a solid material, which contains at least one element having an atomic number of 45 to 56, as an image evaluation pattern simulating a contrast medium.

As described above, the phantom 50 of each of the above embodiments has a solid material containing an element based on the k absorption edge of iodine as an image evaluation pattern simulating a contrast medium. For example, in the case of evaluating the contrast imaging function of the mammography apparatus 10 using a phantom into which a liquid contrast medium is injected as in the conventional technique, there may be a procedure in which a prepared liquid contrast medium is injected into a desired position in the phantom, a radiographic image is then captured with the phantom as a subject, and then the injected contrast medium is discarded. In this case, the amount of contrast medium into the phantom may vary. In addition, the user may feel bothersome due to a plurality of time-consuming steps.

In contrast, in the phantom 50 of the present embodiment, as described above, the image evaluation pattern simulating a contrast medium is a solid material, and can be built into the phantom. Therefore, it is possible to improve the convenience in evaluating the contrast imaging function of the mammography apparatus 10.

In addition, since the phantom 50 of the present embodiment can add the evaluation of the contrast imaging function to the image evaluation pattern used for the evaluation of image quality evaluation items different from the evaluation of the contrast imaging function, it is possible to evaluate a larger number of image quality evaluation items with one phantom 50.

It is needless to say that the elements contained in the solid material, which is an image evaluation pattern simulating the contrast medium contained in the phantom 50, and the manufacturing method are not limited to those in the above-described embodiments and can be changed depending on the situation without departing from the gist of the present invention.

Figure 8:
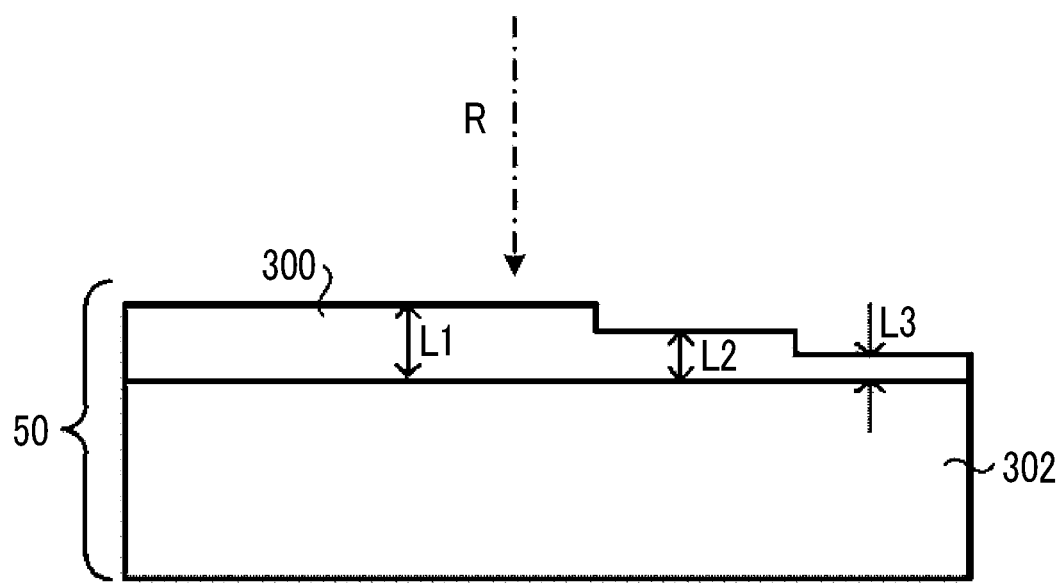
FIG. 8 is a side view showing the configuration of an example of a phantom of another embodiment.

For example, as in a phantom 50 shown in FIG. 8, a sheet 300 formed by molding a resin kneaded with barium sulfate powder may be disposed on the phantom 302 (on the radiation source 29 side). FIG. 8 shows a side view as seen from a direction crossing the incidence direction of the radiation R. In the phantom 50 shown in FIG. 8, the thickness of the sheet 300 in the incidence direction of the radiation R is set to a plurality of thicknesses (thicknesses L1, L2, and L3) according to the concentration of the contrast medium.

The imaging processing or the image quality evaluation processing executed in a case where the CPU executes software (program) in each of the embodiments described above may be executed by various processors other than the CPU. As processors in this case, a programmable logic device (PLD) whose circuit configuration can be changed after manufacture, such as a field-programmable gate array (FPGA), and a dedicated electric circuit that is a processor having a dedicated circuit configuration for executing specific processing, such as an application specific integrated circuit (ASIC), are exemplified. The imaging processing or the image quality evaluation processing may be executed by one of these various processors, or may be executed by a combination of two or more processors of the same type or different types (for example, a plurality of FPGAs and a combination of a CPU and an FPGA). More specifically, the hardware structure of these various processors is an electric circuit in which circuit elements, such as semiconductor elements, are combined.

In each of the above embodiments, the form has been described in which various programs stored in the controller 60 of the mammography apparatus 10 and the controller 70 of the console 6 are stored (installed) in advance in the ROMs (60B, 70B) of the controller 60 and the controller 70. However, the present invention is not limited thereto. The imaging processing program and the image display processing program may be provided in a form recorded on a recording medium, such as a compact disk read only memory (CD-ROM), a digital versatile disk read only memory (DVD-ROM), and a universal serial bus (USB) memory. Alternatively, the imaging processing program and the image evaluation processing program may be downloaded from an external apparatus through a network.

In addition, the configurations, operations, and the like of the radiographic image capturing system 1, the console 6, the mammography apparatus 10, the phantom 50, and the like described in the above embodiments are merely examples, and it is needless to say that these can be changed according to the situation without departing from the gist of the present invention. It is needless to say that the embodiments described above may be appropriately combined.

The disclosure of Japanese Patent Application No. 2017-145849 filed on Jul. 27, 2017 is entirely incorporated in this specification by reference.

All documents, patent applications, and technical standards described in this specification are incorporated in this specification to the same extent as in a case where the incorporation of individual documents, patent applications, and technical standards by reference is described specifically and individually.

EXPLANATION OF REFERENCES

1: radiographic image capturing system
6: console
10: mammography apparatus
11: radiation detector
12: imaging unit
14: base unit
16: imaging table
18: holding unit
20: compression plate
22: support unit
24: imaging surface
26: support arm
28: radiation emission unit
29: radiation source
42: Rh filter
44: Cu filter
50, 302: phantom
60, 70: controller
60A, 70A: CPU
60B, 70B: ROM
60C, 70C: RAM
62, 72: storage unit
64, 74: I/F unit
66: operation panel
69, 83: bus
76: display unit driving unit
78: display unit
80: operation input detection unit
82: operation unit
100, 100A, 100B, 102, 104, 106, 108, 200, 202, 204 image evaluation pattern
103: disk
300: sheet
R: radiation

What is claimed is:

1. A radiographic image capturing system, comprising:
a mammography apparatus that emits radiation having a first energy to a subject and captures a first radiographic image with a radiation detector and emits radiation having a second energy greater than the first energy to the subject and captures a second radiographic image with the radiation detector and that captures the first radiographic image and the second radiographic image with a breast in a state in which a contrast medium using iodine is administered; and
a phantom for evaluation of the mammography apparatus that has a solid material containing at least one element, which has an atomic number of 45 to 56, as an image evaluation pattern simulating the contrast medium.

2. A phantom for evaluation of a mammography apparatus, comprising:
a solid material containing at least one element, which has an atomic number of 45 to 56, as an image evaluation pattern simulating a contrast medium using iodine.

3. An evaluation method for a mammography apparatus, comprising:
a step in which a phantom for evaluation of the mammography apparatus having a solid material containing at least one element, which has an atomic number of 45 to 56, as an image evaluation pattern simulating a contrast medium using iodine is irradiated with radiation having a first energy from the mammography apparatus and a first radiographic image is captured by a radiation detector;

a step in which the phantom is irradiated with radiation having a second energy greater than the first energy and a second radiographic image is captured by the radiation detector; and a step of generating a third radiographic image in which the solid material is emphasized from the first radiographic image and the second radiographic image.

* * * * *